United States Patent [19]
Ashby et al.

[11] Patent Number: 5,984,934
[45] Date of Patent: Nov. 16, 1999

[54] LOW-PROFILE SURGICAL CLIP

[75] Inventors: Mark P. Ashby, Laguna Niguel; Gary M. Johnson, Mission Viejo; Luis Urquidi, Laguna Hills, all of Calif.

[73] Assignee: Applied Medical Resources Corporation, Laguna Hills, Calif.

[21] Appl. No.: 08/949,126

[22] Filed: Oct. 10, 1997

[51] Int. Cl.⁶ .................................................. A61B 17/04
[52] U.S. Cl. ......................... 606/151; 606/157; 606/158
[58] Field of Search ................................... 606/157, 158, 606/151

[56] References Cited

U.S. PATENT DOCUMENTS

| | | | |
|---|---|---|---|
| 3,182,373 | 5/1965 | Strand | 24/263 |
| 3,509,882 | 5/1970 | Blake | 606/158 |
| 3,510,923 | 5/1970 | Blake | 606/158 |
| 3,579,751 | 5/1971 | Jonckheere | 24/252 |
| 4,324,248 | 4/1982 | Perlin | 128/325 |
| 4,407,285 | 10/1983 | Perlin | 128/325 |
| 4,681,109 | 7/1987 | Arroyo | 128/335 |
| 4,796,625 | 1/1989 | Kees, Jr. | 128/325 |
| 4,815,466 | 3/1989 | Perlin | 128/325 |
| 4,817,604 | 4/1989 | Smith, III | 128/346 |
| 4,832,027 | 5/1989 | Utz | 126/337 |
| 4,931,058 | 6/1990 | Copper | 606/158 |
| 4,971,055 | 11/1990 | von Zeppelin | 606/158 |
| 4,976,721 | 12/1990 | Blasnik et al. | 606/157 |
| 5,042,118 | 8/1991 | Rubik | 24/523 |
| 5,074,870 | 12/1991 | von Zeppelin | 606/158 |
| 5,103,839 | 4/1992 | Shichman | 128/898 |
| 5,142,776 | 9/1992 | Neely | 29/859 |
| 5,653,720 | 8/1997 | Johnson et al. | 606/151 |

FOREIGN PATENT DOCUMENTS

| | | | |
|---|---|---|---|
| 43-2743 | 6/1991 | European Pat. Off. | A61B 17/08 |
| 2644-056 | 9/1990 | France | A61B 17/28 |
| 2 124 502 | 2/1984 | United Kingdom | A61B 17/12 |

*Primary Examiner*—Gary Jackson
*Attorney, Agent, or Firm*—Richard L. Myers

[57] ABSTRACT

A surgical clip includes a first jaw and a second jaw relatively movable in a first direction between a first relatively proximate position and a second relatively spaced position. The jaws in the second position have a predetermined dimension in the first direction. The clip has an overall maximum dimension in the first direction which is not greater than about the predetermined dimension of the jaws in the second position. A spring under tension is housed in a telescoping barrel and coupled between the first and second jaws for biasing the jaws to the first position.

21 Claims, 7 Drawing Sheets

LOW-PROFILE SURGICAL CLIP

BACKGROUND OF THE INVENTION

1. Field of The Invention

This invention relates generally to surgical clips and more specifically to surgical clips having rigid parallel jaws that are biased to a closed position by a spring.

2. Discussion of the Prior Art

Surgical clips are used to inhibit fluid flow in a body conduit such as a blood vessel. More commonly the clips are applied to totally occlude a blood vessel and thereby inhibit the flow of blood beyond the clip.

In the past, surgical clips have been formed with generally rigid parallel jaws, each attached to a respective barrel portion. These barrel portions have been telescopically movable relative to each other to house a compression spring. Pinching the barrel portions together has opposed the bias on the compression spring and resulted in opening the jaws of the clip. When the barrel portions are released, the compression spring automatically biases the barrel to an expanded configuration and biases the jaws into a closed state.

These clips of the past have had a very high profile which has been dictated by the length of the barrel. When the barrel has been pinched to a low-profile to compress the spring and open the jaws, the height of the barrel has been generally equivalent to the height of the jaws. However, when the barrel is released and the spring expands, the barrel moves to a relatively high configuration as the jaws move to the closed state.

Finger tabs have been attached to the barrel portion generally at their outer-most extremities. Consequently, separation of the finger tabs has been generally equivalent to the height of the barrel. With the distance separating the tabs generally equivalent to the distance separating the jaws, the open state has presented the lowest profile for the clip. As the jaws approach a closed state, the tabs separate even further so that the overall profile of the clip is generally dictated by the height of the tabs.

This configuration of the surgical clips of the prior art has made them particularly unsuited for use in the working channels of access devices such as trocars and endoscopes. Even when elongate surgical clip appliers have been used, the relatively high profile of the barrel portions and tabs has been even further increased. Since the arms of the appliers must necessarily engage the barrel portions and tabs on outer surfaces, the use of appliers only increases the height of the applier/clip combination.

SUMMARY OF THE INVENTION

These deficiencies in the surgical clips of the prior art are overcome with the present invention which includes rigid parallel jaws and telescoping barrel portions which are joined by a tension spring. In some cases, the barrel portions are associated with upper and lower finger tabs which are coupled to the lower and upper jaws, respectively. Moving these tabs together opposes the bias on the tension spring and moves the jaws to the open state. When the tabs are released, they expand to their maximum height as the tension spring moves the jaws to their closed state.

Importantly, the highest profile of the clip is dictated generally by the separation of the jaws, not the height of the barrel or the separation of the tabs. For example, when the jaws are in an open state, the barrel portions move to a height which is generally equivalent to the separation of the jaws. Notably, in this open state, the tabs are in a closely proximate, perhaps contacting, relationship. Thus, in the open state, the barrel portions and jaws define the height of the clip, since the tabs are in their lowest profile. This configuration facilitates use with a clip applier which can engage the outer surfaces of the tabs without increasing the overall height of the clip/applier combination. Even when the jaws are in the closed state, and the tabs are separated, the height of the clip is not greater than the height of the jaws in the open state.

In one aspect of the invention, a surgical clip includes a first jaw and a second jaw coupled to the first jaw. The first and second jaws are relatively movable in aft direction between a first relatively proximate position and a second relatively spaced position. The first and second jaws in the second position have a predetermined dimension in the first direction. The clip has a maximum dimension in the first direction which is not greater than about the predetermined dimension of the first and second jaws in the second position.

In another aspect of the invention, a surgical clip includes a first jaw, and a second jaw movable relative to the first jaw between a first proximate position and a second spaced position. A spring having a compressed state and an expanded state, and properties for biasing the spring to the compressed state, is coupled between the first jaw and the second jaw to bias the first jaw and the second jaw to the first position. In another aspect of the invention, a surgical clip includes a first jaw and a second jaw movable relative to the first jaw between a first proximate position and a second spaced position. A spring under tension is coupled to the first and second jaws and has properties for biasing the first and second jaws to the first position. A first tab and a second tab have fixed relationships with the first jaw and second jaw, respectively. The first jaw is movable relative to the second tab to oppose the bias of the spring and move the first and second jaws to the second position. The first jaw is disposed in a first direction relative to the second jaw and the first tab is disposed in the first direction relative to the second tab.

In a further aspect of the invention, the first tab and second tab are relatively movable between a third proximate position and a fourth spaced position. The first jaw is disposed in a first direction relative to the second jaw. The first tab is disposed in a second direction opposite to the first direction relative to the second tab. In this case, the first and second jaws are movable to the second position when the first and second tabs are moved to the third position.

These and other features and advantages of the invention will become more apparent with a description of preferred embodiments and reference to the associated drawings.

DESCRIPTION OF THE DRAWINGS

FIG. 11 to FIG. 15 are assembly views of the clip illustrated in FIG. 8;

DESCRIPTION OF PREFERRED EMBODIMENTS

Figure 1:
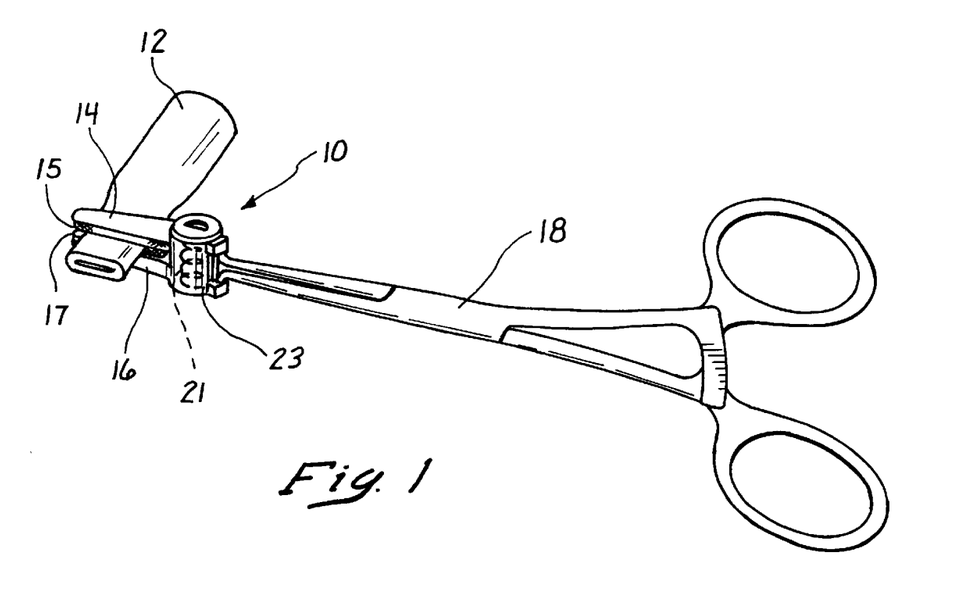
FIG. 1 is a perspective view illustrating a clip of the present invention, operable by a clip applier to occlude a body conduit.

A low-profile surgical clip is illustrated in the perspective view of FIG. 1 and designated generally by the reference numeral 10. The clip 10 is illustrated in an operative position where it is disposed to occlude a body conduit such as a blood vessel 12. The clip 10 includes a pair of opposing generally parallel jaws 14 and 16 which are movable between an open state and the illustrated closed state by operation of a clip applier 18. Each of the jaws 14 and 16 can be provided with an insert 15, 17, respectively, which reduces trauma and increases traction with the vessel 12. The jaws 14, 16 of the clip 10 are biased to the closed state by a spring 21 which is housed in a barrel 23. The spring 21 has a compact or compressed configuration in a relaxed state and an expanded, elongated configuration in an axially tensioned state. These tension characteristics of the spring 21 add significant advantages to the clip 10 in a manner described in greater detail below.

Figure 2:
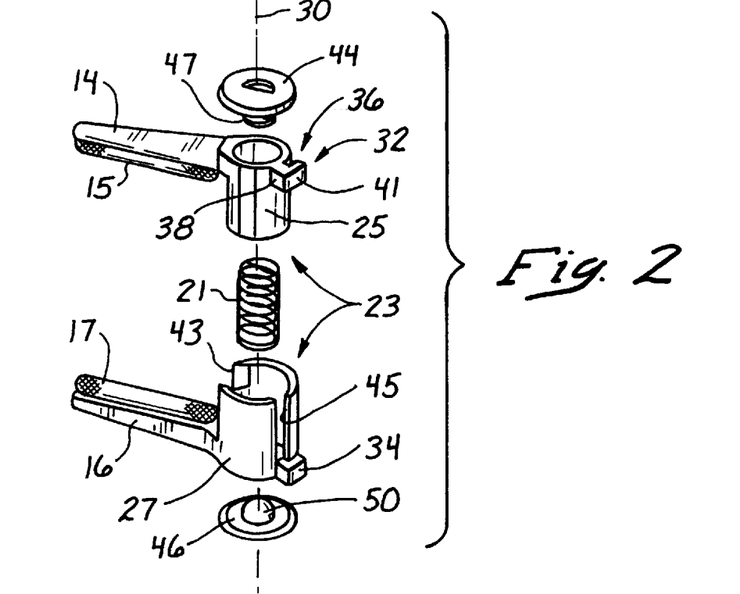
FIG. 2 is an expanded view of the clip illustrated in FIG. 1.

The structural elements of this particular embodiment are best illustrated in the exploded view of FIG. 2, where it can be seen that the barrel 23 is formed from a pair of telescoping barrel portions 25 and 27. In this embodiment, the barrel portion 25 is integral with the jaw 14 and the barrel portion 27 is integral with the jaw 16. Both of the barrel portions 25 and 27 have a generally hollow, cylindrical configuration which extends along an axis 30 of the barrel 23. As perhaps best illustrated in FIG. 3, the barrel portion 27 is sufficiently large to receive the barrel portion 25 in a telescoping relationship; the barrel portion 25 is sufficiently large to receive the spring 21.

Engagement tabs 32 and 34 are provided in a fixed relationship with each of the barrel portions 25 and 27, respectively. The engagement tab 32 associated with the barrel portion 25 is provided with a groove or slot 36 which forms a rail 38 and a flange 41. A pair of axial slots 43 and 45 are formed in the cylindrical wall of the barrel portion 27. The slot 45 is sized and configured to receive the rail 38 of the tab 32, and the slot 43 is configured to receive the jaw 16 as the barrel portion 25 moves along the axis 30 in a telescoping relationship with the barrel portion 27.

With the tab 32 having a fixed relationship to the jaw 14 and the tab 34 having a fixed relationship with the jaw 16, the telescoping movement of the barrel portions 25 and 27 results in movement of the jaws 14 and 16 and the tabs 32 and 34 between proximate and spaced positions. When the jaws 14, 16 and the tabs 32, 34 are spaced, the clip 10 is in an open state best illustrated in the side-view of FIG. 4. When the jaws 14, 16 and the tabs 32, 34 are proximate, the clip 10 is in a closed state best illustrated in the cross-sectional view of FIG. 3. This embodiment also includes end caps 44 and 46, each having an associated spring engagement flange 47, 50 as best illustrated in FIG. 2.

The clip 10 in this embodiment is assembled by initially inserting the smaller barrel portion 25 into the larger barrel portion 27. During this step, the jaws 14, 16 are aligned and the rail 38 is positioned within the slot 45. One end of the tension spring 21 can be attached to the flange 50 of the end cap 41 and the spring 21 inserted into the smaller barrel portion 25. The tension spring 21 can then be axially expanded to permit attachment of the opposite end of the spring 21 to the flange 47 of the end cap 44. The end caps 44 and 46 can then be appropriately glued or otherwise fixed to the associated barrel portions 25 and 27.

Figure 3:
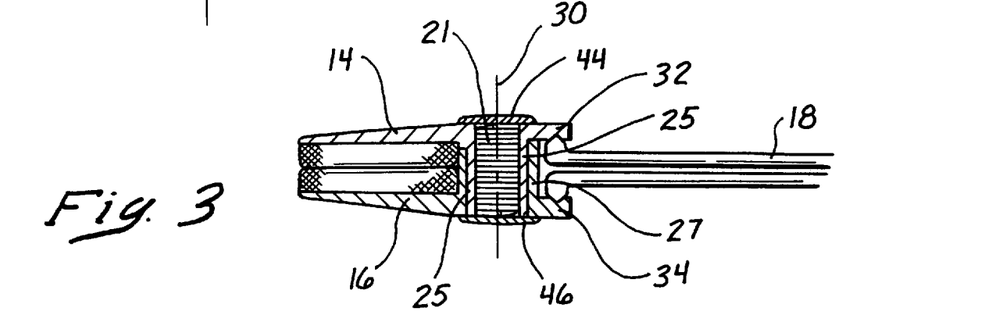
FIG. 3 is a radial cross-section view of the clip illustrated in FIG. 1.

In this embodiment, the tension spring 21 biases the associated end caps 44, 46, the associated barrel portions 25, 27, and the associated jaws 14, 16 to their proximate positions. As noted, these proximate positions are associated with the closed state of the clip 10 as illustrated in FIG. 3. The clip 10 is movable to the open state by inserting jaws of the clip applier 18 between the engagement tabs 32, 34, and operating the applier 18 to separate those tabs 32, 34. This opposes the bias on the spring 21, separates the end caps 43, 45 and the jaws 14, 16, and moves the clip 10 to the open state as illustrated in FIG. 4.

Figure 4:
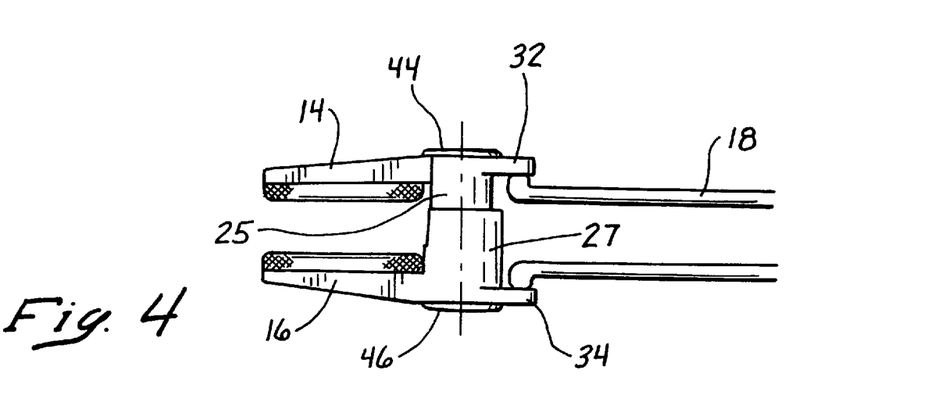
FIG. 4 is a side-elevation view of the clip illustrated in FIG. 1.

With particular reference to FIGS. 3 and 4, it will be noted that the clip 10 always has a height which is generally dictated by the height of the jaws 14, 16. In the closed state illustrated in FIG. 3, the clip 10 is biased to the closed state and has a very low profile. In the open state illustrated in FIG. 4, the clip 10, of course, has a higher profile, but this profile is generally not greater than the height of the jaws 14, 16.

Figure 5:
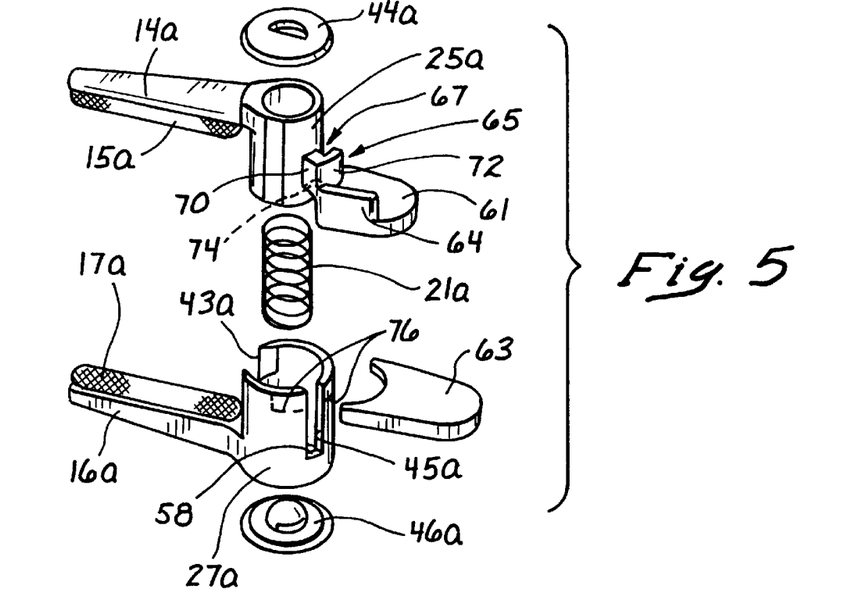
FIG. 5 is an expanded view of an additional embodiment of the clip of the present invention.
Figure 6:
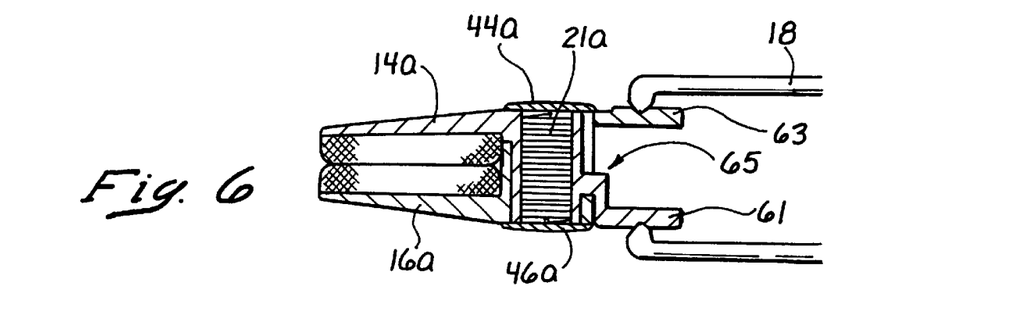
FIG. 6 is a radial cross-section view of the clip illustrated in FIG. 5.
Figure 7:
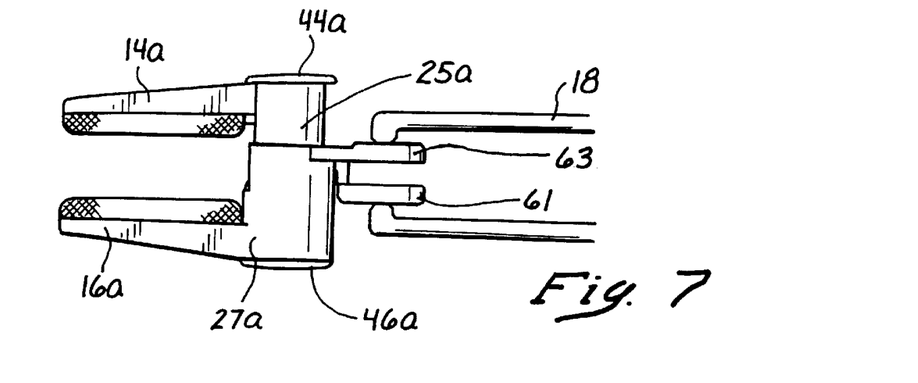
FIG. 7 is a side-elevation view of the clip illustrated in FIG. 5.

An additional embodiment of the invention is illustrated in FIGS. 5–7. In these figures, structural elements which are similar to those previously discussed will be designated by the same reference numeral followed by the lower-case letter "a". Thus, in FIG. 5, the clip 10a includes the jaw 14a and insert 15a which are associated with the barrel portion 25a and end cap 43a. It also includes the jaw 16a and insert 17a which are associated with the barrel portion 27a and end cap 45a. In the manner previously discussed, this embodiment includes the tension spring 21a, as well as the axial slots 43a and 45a in the barrel portion 27a. In this case, the slot 45a extends along a substantial length of the barrel portion 27a, but terminates at a surface 58 at the bottom of the slot 45a.

This embodiment of FIG. 5 also differs from that previously discussed primarily in the provision of a pair of finger tabs 61 and 63, which are associated with the barrel portions 25a and 27a, respectively. The finger tab 61 is provided with an axial stop 64 and coupled to the barrel portion 25a by a connector 65. This connector 65 includes a slot 67 which is defined by a rail 70 and flange 72. In this case, the rail 70 extends axially terminating in a bottom surface 74. It also extends radially so that the flange 72 is spaced from the outer surface of the barrel portion 25a.

Assembly of the clip 10a can be accomplished by initially inserting the barrel portion 25a into the barrel portion 27a. During this step, the rail 70 is positioned within the slot 45a and the surface 74 of the rail 70 approaches the surface 58 defining the slot 45a. With the rail 70 located within the slot 45a, the finger tab 63 can be glued or otherwise fixed to the barrel portion 27a, for example, at the position indicated by dotted lines 76. The spring 21a can then be mounted within the telescoping barrel portions 25a, 27a, and the end caps 44a and 46a glued into place in the manner previously discussed. With particular reference to FIGS. 6 and 7, it will be noted that in the clip 10a of this embodiment, the upper jaw 14a is associated with the lower finger tab 61 and the lower jaw 16a is associated with the upper finger tab 63.

As in the previous embodiment, the spring 21a biases the clip 10a to the closed state illustrated in FIG. 6. This bias of the spring 21a must be opposed to move the clip 10a to the open state illustrated in FIG. 7. In this embodiment, movement of the jaws 14a and 16a to the open state is accomplished by moving the finger tabs 61 and 63 into close proximity as illustrated in FIG. 7. Thus, force can be exerted on the outer surfaces of the tabs 61 and 63 in order to open the jaws 14a and 16a. Since a squeezing force is much more natural between the thumb and fingers of the human hand, this clip 10a is particularly adapted for manipulation by the fingers of the user. The tabs 61 and 63 are squeezed together to open the jaws 14a, 16a, and released to permit the bias of the spring 21a to close the jaws 14a, 16a and occlude the vessel 12 (FIG. 1).

Figure 8:
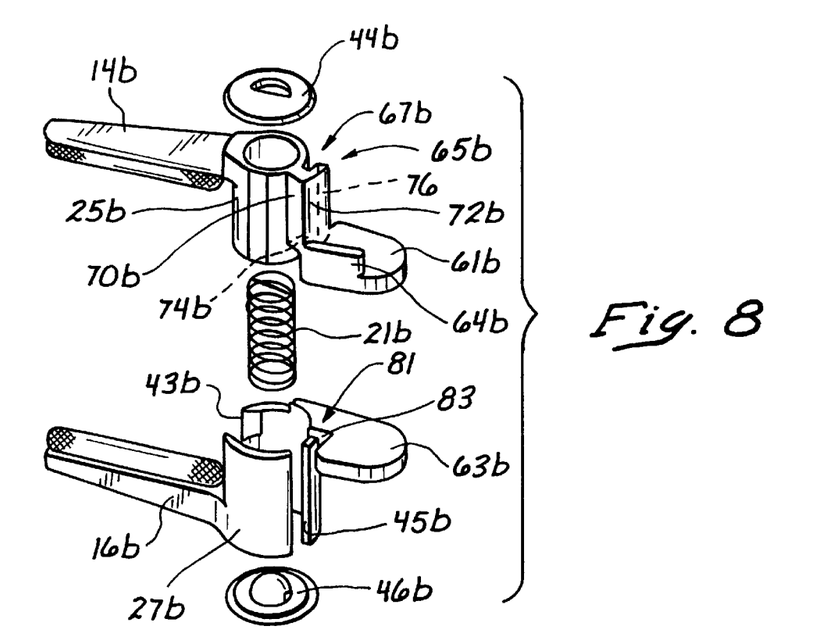
FIG. 8 is an expanded view of a further embodiment of the clip of the present invention.
Figure 9:
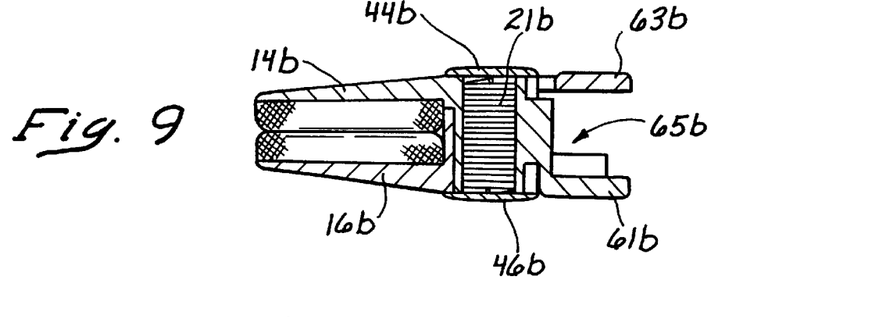
FIG. 9 is a radial cross-section view of the clip illustrated in FIG. 8.
Figure 10:
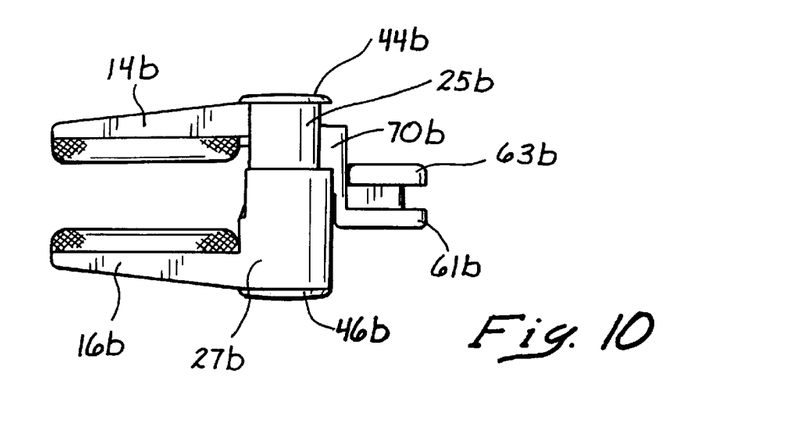
FIG. 10 is a side-elevation view of the clip illustrated in FIG. 8.

In another embodiment of the invention illustrated in FIGS. 8–15, structural elements which are similar to those previously discussed will be designated by the same reference numerals followed by the lower-case letter "b". Thus, the upper jaw 14b is associated with the barrel portion 25b, tab 61b, stop 64b, and connector 65b. Also illustrated in FIG. 8 are the rail 70b and flange 72b which define the slot 67b. In a similar manner, the lower jaw 16b is associated with the barrel portion 27b which is formed with the slots 43b and 45b. In this embodiment, it will be noted that the rail 70b and flange 72b extend along a substantial length, more than half, of the barrel portion 25b.

The finger tab 63b associated with the lower jaw 16b differs from that previously discussed in that it is fixed to or molded integral with the bottom barrel portion 27b prior to assembly. The finger tab 63b is not disposed over the slot 45b, but rather is configured with a notch 81 which is defined in part by a surface 83 that faces the slot 45b. In this case, the rail 70b is associated with the bottom surface 74b, while the flange 72b is associated with an outer surface 76.

The embodiment of FIG. 8 is of particular interest since it provides for operation of the clip 10b using a squeezing motion, but avoids the step of gluing, or otherwise attaching, the finger tab 63 during assembly of the clip.

Figure 11:
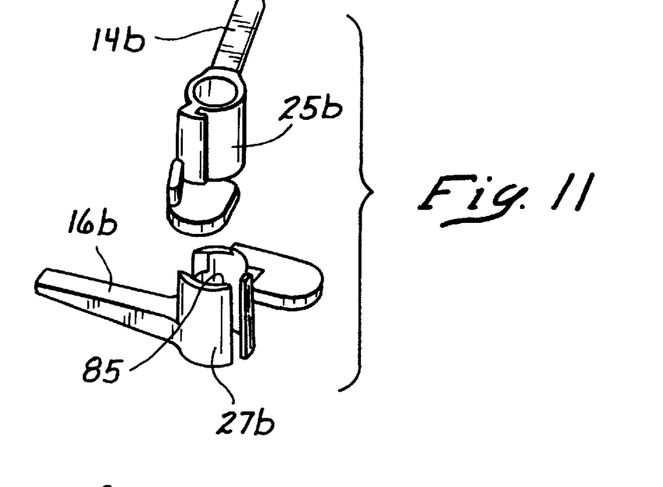
FIG. 11 is a perspective view illustrating the clip as two separated sub-assemblies, each including a barrel portion.

Various steps in the process for assembling the clip 10b are illustrated in FIGS. 11–15. In FIG. 11, the jaws 14b, 16b, and barrel portions 25b, 27b are illustrated in a spaced relationship. During the assembly process, an upper surface 85 associated with the lower barrel portion 27b is of particular interest.

Figure 12:
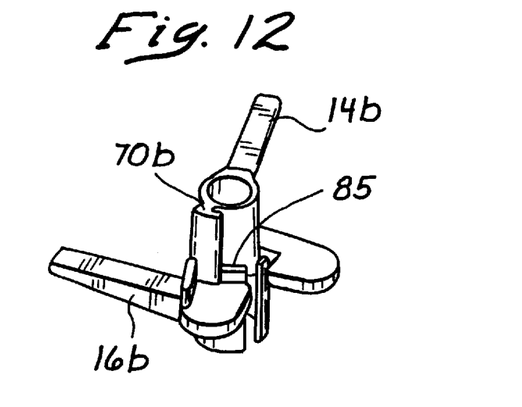
FIG. 12 is a perspective view illustrating the clip in an initial step of assembly.
Figure 13:
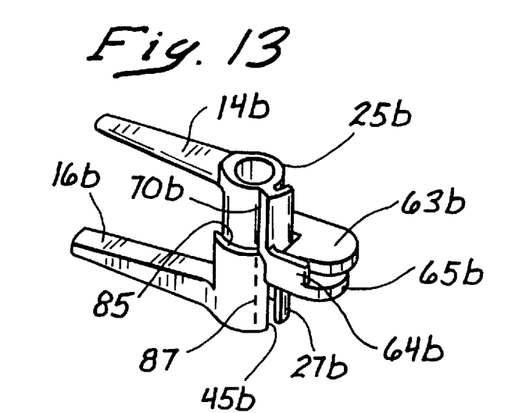
FIG. 13 is a perspective view illustrating the sub-assemblies rotated relative to each other to an interference fit.

In an initial step of the assembly process, the barrel portion 25b is inserted into the barrel portion 27b and the surface 74b (FIG. 8) associated the rail 70b is brought into contact with the surface 85. It will be noted that initially the jaws 14b and 16b are angularly spaced a significant distance as illustrated in FIG. 12. Rotating the jaw 14b into closer proximity to the jaw 16b, as illustrated in FIG. 13, will bring the stop 64b into an interference fit with the finger tab 63b. This interference prohibits the parallel orientation of the jaws 14b, 16b because the rail 70b is not seated in the slot 45b. This interference fit is illustrated in FIG. 13 where it can be seen that the lateral surface of the rail 70b extends along a dotted line 87, rather than along the slot 45b.

At this point in the assembly process, further rotational movement of the barrel portion 25b relative to the barrel portion 27b is inhibited by the interference fit between the stop 64b and the finger tab 63b. Further axial movement of the barrel portion 25b into the barrel portion 27b is inhibited by the interference between the rail 70b and the surface 85b.

Figure 14:
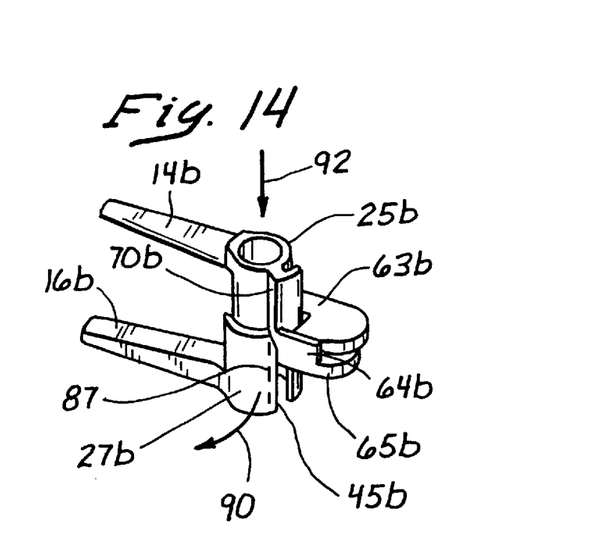
FIG. 14 is a perspective view illustrating one of the barrel portions bent to overcome the interference fit.
Figure 15:
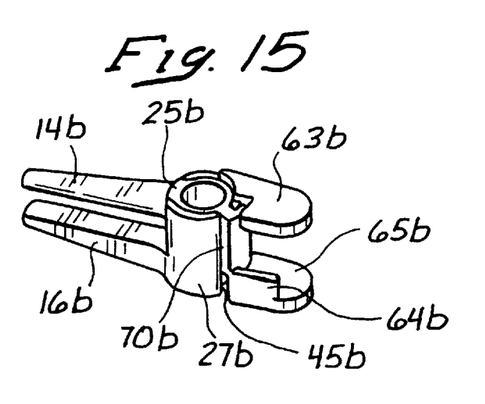
FIG. 15 is a perspective view illustrating the barrel portions axially telescoped to their final orientation.

In the next step of the process, the slot 45b is expanded by forcing, moving, or bending the wall of the barrel portion 27b outwardly as shown by an arrow 90 in FIG. 14. During this bending step, the slot 45b expands as it approaches the line 87 associated with the rail 70b. When this line 87 extends into the slot 45b, the barrel portion 25b is no longer inhibited from movement in the axial direction. Thus, during the bending step, the barrel portion 25b can be moved axially along an arrow 92 as the rail 70b moves along the slot 45b. It will be noted that the angular interference fit between the stop 64b and the finger tab 63b does not inhibit this axial movement of the barrel portion 25b along the arrow 92.

As the rail 70b moves into the slot 45b, the stop 64b also moves axially with respect to the tab 63b. Eventually, this stop 64b clears the tab 63b and the inherent force of the bent wall forces the rail 70b and finger tab 65b into its final operative position primarily characterized by a parallel orientation of the jaws 14b and 16b. In this final orientation, illustrated in FIG. 15, the stop 64b associated with the finger tab 65b is disposed axially, beneath the finger tab 63b, and the rail 70b is free to slide axially a limited distance within the slot 45b. This sliding distance is limited by the interference fit which naturally occurs when the finger tab 63b comes into contact with the upper surface of the stop 64b.

Operation of the clip 10b is similar to that of the clip 10a as can be seen from a comparison of FIGS. 9, 10 and FIGS. 6, 7, respectively. In general, the clip 10 is initially moved to an open state by squeezing the finger tabs 61 and 63 into proximity. This can be accomplished either with the fingers of the user or with the clip applier 18. After the open jaws 14b, 16b have been moved into operative position around the vessel 12 (FIG. 1), the tab 61, 63 can be released thereby permitting the tension spring 21 to bias the jaws 14, 16 to the closed state illustrated in FIG. 9. It will be noted that in both the open and closed states, the height of the clip 10 is dictated generally by the particular height of the jaws 14, 16. Although the height of the barrel portions 25, 27 generally follows this particular height, the height of the tabs 61, 63 is generally never greater than this particular height.

Figure 16:
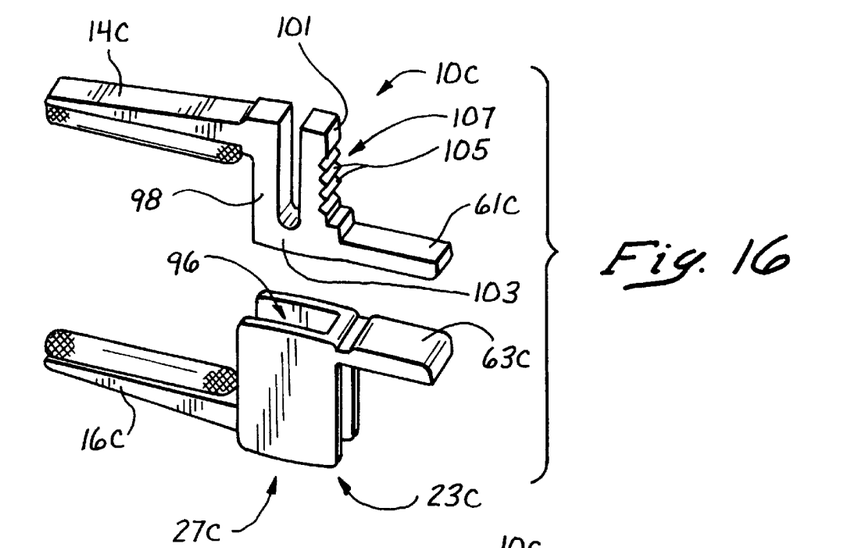
FIG. 16 is an exploded view of a further embodiment of the clip of the present invention.
Figure 17:
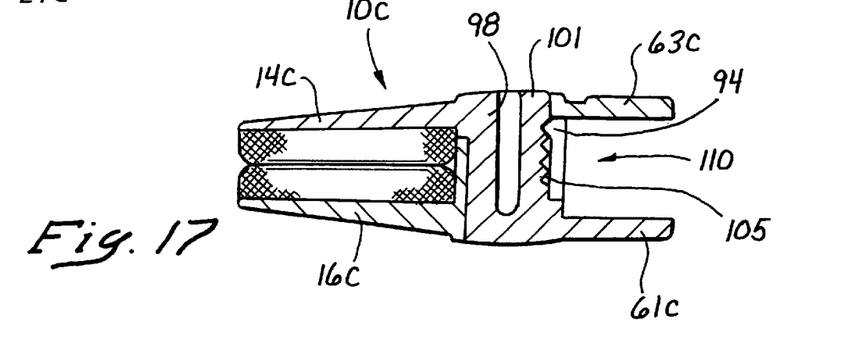
FIG. 17 is a radial cross-section view of the clip illustrated in FIG. 16.
Figure 18:
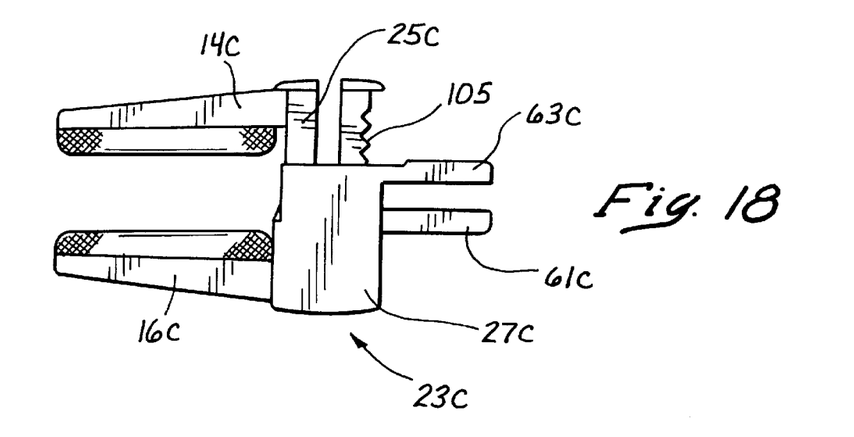
FIG. 18 is a side-elevation view of the clip illustrated in FIG. 16.

A ratchet embodiment of the invention is illustrated in FIGS. 16–18, where elements similar to those previously discussed are designated by the same reference numeral followed by the lower-case letter "c". Thus, FIG. 16 illustrates the clip 10c to include the jaws 14c, 16c, as well as the tabs 61c and 63c. This embodiment differs from those previously discussed in that the barrel 23c has a generally rectangular configuration providing the clip 10c with a narrow, as well as a low-profile, configuration. The barrel 23c has barrel portions 25c and 27c which differ in several respects from those previously discussed. In addition to the rectangular configuration, the barrel portion 27c is provided with a detent 94 which extends into an interior channel 96 of the barrel portion 27c. The barrel portion 25c has a generally U-shaped configuration with a pair of legs 98, 101 joined by a cross-member 103. In this embodiment, the leg 98 is coupled to the jaw 14c while the leg 101 is coupled to the tab 61c. The cross-member 103 is disposed at one end of the legs 98 and 101 so that the leg 101 is free to bend slightly toward the leg 98. Importantly, the surface of the leg 101 which faces proximally, in the direction of the tab 61c, is provided with a series of teeth 105 which define a plurality of slots 107.

The clip 10c is easily assembled by inserting the tab 61c into the channel 96 of the barrel portion 27c. Pivoting the jaw 14c counterclockwise in FIG. 16 enables the barrel portion 25c to be moved further into the channel 96. When fully assembled, the clip 10c is movable between a closed state and an open state, as illustrated in FIGS. 17 and 18, respectively. In the closed state illustrated in FIG. 17, the jaws 14c and 16c are proximate and the tabs 61c and 63c are maximally separated. In the open state illustrated in FIG. 18, the jaws 14c, 16c are maximally separated, and the tabs 61c and 63c and minimally separated. Between these two ultimate positions, the teeth 105 and the detent 94 form a ratchet or detent mechanism 110 which provides a predetermined degree of resistance at various positions between the extremes.

It is of particular advantage that both of the extreme states illustrated in FIGS. 17 and 18 can be achieved with a squeezing motion. In order to open the jaws 14c, 16c from the closed state illustrated in FIG. 17, one merely engages the tabs 61c, 63c and squeezes them into proximity, as illustrated in FIG. 11. In order to close the jaws 14c, 16c from the open state illustrated in FIG. 18, one merely engages the outer surfaces of the barrel portions 25c and 27c and squeezes these surfaces into proximity as illustrated in FIG. 17. This squeezing motion is further facilitated by the configuration of the clip 10c wherein the tabs 61c and 63c can be engaged when they are near the maximum height of the clip, and the barrel portions 25c and 27c can also be engaged when they are near the maximum height of the clip 10c.

In this embodiment, it can also be seen that the maximum height of the clips 10c is generally defined by the maximum height of the jaws 14c and 16c. This height is dictated by the outer surfaces of the jaws 14c and 16c, which may be tapered outwardly to the maximum height in proximity to the barrel 25c. Generally speaking, although the barrel 25 and the caps 44 and 46 in several embodiments (such as FIG. 8) may increase this maximum height slightly, it can still be appreciated that in general the height of the clip 10 is dictated by the height of the jaws 14, 16.

Figure 19:
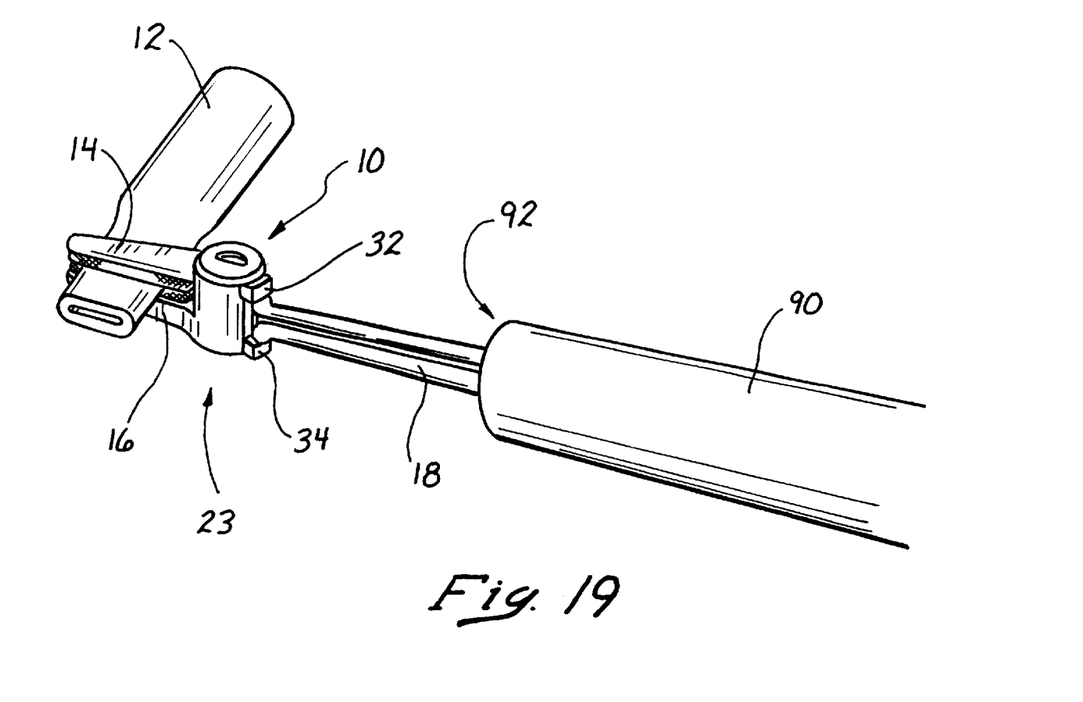
FIG. 19 is a perspective view of one embodiment of the clip of the present invention illustrating insertion of the low-profile clip through the working channel of a trocar.

Certainly one of the primary advantages associated with the present clip construction is its low profile. In several embodiments, this feature is facilitated by provision of a tension spring which enables the biasing action to be produced within a barrel of reduced height. This feature is best illustrated in FIG. 19 wherein the clip 10 is adapted for insertion through a tube 94 having a working channel 96. The tube 94 may be an endoscope, a trocar, or any other access device extending across a body wall. With a clip 10 having a maximum height dictated generally by the height of the jaws 14, 16, the barrel 25 does not provide any substantial increase in height. In a preferred embodiment, the clip 10 has jaws that are approximately ¾" in length and the height of the clip in the closed state is about ⅜". This facilitates use of the clip 10 in a trocar or tube 94 having a working channel 96 with an 11-millimeter diameter. An additional advantage associated with the present clip construction is its ability to maintain jaw symmetry and linear orientation about the axis of the clip applier. This is of particular advantage when used through a trocar or used to access a remote site.

There are many variations in the foregoing concept which will be apparent to those skilled in the art. Certainly, materials can vary significantly, although in the preferred embodiment elements other than the spring 21 are formed by injection-molding polycarbonate plastic. In this embodiment, the spring 21 is formed of stainless steel wire having a diameter of about 0.018". The spring is wound to a diameter of about 0.200" and a length of about 0.33" to provide a spring constant of about 1 pound per inch. The inserts 15 and 17 can also vary widely in different embodiments of the invention. In a preferred embodiment, the inserts 15, 17 have a foam rubber substrate, but are covered with a mesh structure which facilitates traction with the vessel 12.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

We claim:

1. A surgical clip, comprising:

a first jaw;

a second jaw coupled to the first jaw;

the first jaw and second jaw being relatively movable in a first direction between a first relatively proximate position and a second relatively spaced position;

the first jaw and second jaw in the second position having a predetermined dimension in the first direction;

the clip having a maximum dimension in the first direction which is not greater than about the predetermined dimension of the first jaw and the second jaw in the second position;

a first tab coupled to the first jaw and movable with the first jaw between the first position and the second position;

a second tab coupled to the second jaw and movable with the second jaw between the first position and the second position;

the first tab and second tab being movable relative to each other between a third proximate position and a fourth spaced position;

the first jaw and the second jaw in the second position having a first outside dimension;

the first tab and the second tab in the fourth spaced position having a second outside dimension not greater than about the first outside dimension of the first jaw and second jaw in the second position;

a barrel extending along an axis generally transverse to the first jaw and the second jaw;

the barrel having a maximum dimension along the axis which is not greater than about the first outside dimension of the first jaw and the second jaw in the second position; and a spring under tension disposed in the barrel and having properties for biasing the jaws to the first position.

2. The surgical clip recited in claim 1, further comprising:

a ratchet assembly providing a predetermined resistance to relative movement of the first jaw and the second jaw, at a plurality of discrete positions between the first position and the second position.

3. The surgical clip recited in claim 1, wherein the first tab and the second tab are spaced from the axis of the barrel.

4. A surgical clip, comprising:

a first jaw;

a second jaw coupled to the first jaw;

the first jaw and second jaw being relatively movable in a first direction between a first relatively proximate position and a second relatively spaced position;

the first jaw and second jaw in the second position having a predetermined dimension in the first direction;

the clip having a maximum dimension in the first direction which is not greater than about the predetermined dimension of the first jaw and the second jaw in the second position;

a first tab coupled to the first jaw and movable with the first jaw between the first position and the second position;

a second tab coupled to the second jaw and movable with the second jaw between the first position and the second position;

the first tab and second tab being movable relative to each other between a third proximate position and a fourth spaced position;

the first jaw and the second jaw in the second position having a first outside dimension;

the first tab and the second tab in the fourth spaced position having a second outside dimension not greater than about the first outside dimension of the first jaw and second jaw in the second position; and the first tab and the second tab being spaced from the axis of the barrel.

5. A surgical clip, comprising:

a first jaw;

a second jaw movable relative to the first jaw between a first proximate position and a second spaced position;

a spring coupled to the first jaw and the second jaw; and the spring having first tension characteristics when the first jaw and the second jaw are in the first proximate position, and second tension characteristics greater than the first tension characteristics when the first jaw and the second jaw are in the second space position.

6. The surgical clip recited in claim 5, further comprising:

a first barrel portion having a fixed relationship with the first jaw;

a second barrel portion having a fixed relationship with the second jaw;

the first barrel portion and the second barrel portion movable relative to each other along a common axis in a telescoping relationship;

the first barrel portion and the second barrel portion defining an interior cavity extending along the axis; and the spring being disposed within the cavity of the first barrel portion and the second barrel portion.

7. The surgical clip recited in claim 6, further comprising:

a first tab having a fixed relationship with the first barrel portion;

a second tab having a fixed relationship with the second barrel portion;

the first tab and second tab being movable relative to each other in spaced relationship with the axis of the first barrel portion and second barrel portion.

8. The surgical clip recited in claim 5, wherein:

the first jaw and the second jaw are movable relative to each other in a first direction between the first position and the second position;

the first jaw and second jaw are separated by a maximum distance in the second position; and the maximum dimension of the clip measured in the first direction is not greater than the maximum distance separating the first jaw and the second jaw in the second position.

9. A surgical clip, comprising:

a first jaw;

a second jaw movable relative to the first jaw between a first proximate position and a second spaced position;

a spring under tension coupled to the first jaw and the second jaw, the spring having properties for biasing the first jaw and the second jaw to the first position;

a first tab having a fixed relationship with the first jaw;

a second tab having a fixed relationship with the second jaw;

the first tab being movable relative to the second tab to oppose the bias of the spring and move the first jaw and the second jaw to the second position;

the first jaw being disposed in a first direction relative to the second jaw; and the first tab being disposed in the first direction relative to the second tab.

10. The surgical clip recited in claim 9, wherein:

the first tab and the second tab are relatively movable between a third proximate position and a fourth spaced position; and the first tab and the second tab are in the fourth spaced position when the first jaw and the second jaw are in the second spaced position.

11. The surgical clip recited in claim 10, wherein:

the first jaw and the second jaw in the second spaced position have a first maximum dimension in the first direction;

the first tab and second tab in the fourth spaced position have a second maximum dimension in the first direction; and the second maximum dimension of the first tab and second tab is not greater than the first maximum dimension of the first jaw and the second jaw.

12. The surgical clip recited in claim 10, further comprising:

a first barrel portion having a fixed relationship with the first jaw and the first tab;

a second barrel portion having a fixed relationship with the second jaw and the second tab;

the first barrel portion and the second barrel portion having a telescoping relationship and an interior cavity sized and configured to receive the spring.

13. A surgical clip, comprising:

a first jaw;

a second jaw movable relative to the first jaw between a first proximate position and a second spaced position;

a spring under tension coupled to the first jaw and the second jaw and biasing the first jaw and the second jaw to the first proximate position;

a first tab having a fixed relationship with the first jaw;

a second tab having a fixed relationship with the second jaw;

the first tab and the second tab being movable relative to each other between a third proximate position and a fourth spaced position;

the first jaw being disposed in a first direction relative to the second jaw; and the first tab being disposed in a second direction opposite to the first direction relative to the second tab.

14. The surgical clip recited in claim 13, wherein:

the first jaw and the second jaw being movable to the second spaced position when the first tab and the second tab are moved to the third proximate position.

15. The surgical clip recited in claim 14, wherein:

the first jaw and the second jaw in the second spaced position have a first dimension measured in the first direction; and the first tab and the second tab in the fourth spaced position have a second dimension measured in the first direction; and the second dimension of the first tab and the second tab is not greater than the first dimension of the first jaw and second jaw.

16. The surgical clip recited in claim 13, further comprising:

a first barrel portion having a fixed relationship with the first jaw and the first tab;

a second barrel portion having a fixed relationship with the first jaw and the second jaw; and the first barrel portion and the second barrel portion have a telescoping relationship and an interior cavity sized and configured to receive the spring.

17. A method for assembling a surgical clip, comprising the steps:

providing a first clip portion having a first jaw, a first barrel portion with a first axis, and an axial rail;

providing a second clip portion having a second jaw, a second barrel portion with a second axis, and an axial slot;

aligning the first axis of the first barrel portion with the second axis of the second barrel portion;

moving the first barrel portion generally axially of the second barrel portion to form a barrel of the clip;

during the first moving step, maintaining the first jaw and the second jaw in a generally angularly spaced relationship;

moving the first barrel portion relative to the second barrel portion from a first position wherein the first jaw and the second jaw are angularly spaced to a second position wherein the first jaw and second jaw are generally angularly aligned; and during the second moving step rotating the first barrel portion with respect to the second barrel portion.

18. The method recited in claim 17, wherein the second moving step further comprises:

expanding the slot of the second barrel portion to receive the rail of the first barrel portion.

19. The method recited in claim 17, wherein the second moving step further comprises after the expanding step, the step of:

sliding the rail of the first barrel portion within the slot of the second barrel portion to move the first barrel portion generally axially of the second barrel portion.

20. The method recited in claim 17, wherein the first moving step comprises the step of:

advancing the first barrel portion relative to the second barrel portion to a first interference fit.

21. The method recited in claim 20, wherein the rotating step includes the step of:

advancing the first barrel portion relative to the second barrel portion to a second interference fit.

* * * * *